(12) United States Patent
Baumgart et al.

(10) Patent No.: US 8,594,403 B2
(45) Date of Patent: Nov. 26, 2013

(54) DATA MANAGEMENT SYSTEM FOR USE IN ANGIOGRAPHIC X-RAY IMAGING

(75) Inventors: John Baumgart, Hoffman Estates, IL (US); Benita Devadas, South Barrington, IL (US); Thomas Ruggiero, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 208 days.

(21) Appl. No.: 13/191,498

(22) Filed: Jul. 27, 2011

(65) Prior Publication Data

US 2012/0114215 A1    May 10, 2012

Related U.S. Application Data

(60) Provisional application No. 61/411,026, filed on Nov. 8, 2010.

(51) Int. Cl.
*G06K 9/00* (2006.01)

(52) U.S. Cl.
USPC ........ 382/130; 345/619; 378/98.12; 382/128; 382/131; 382/132; 382/134; 600/407; 600/431; 600/458

(58) Field of Classification Search
None
See application file for complete search history.

(56) References Cited

U.S. PATENT DOCUMENTS

| | | | |
|---|---|---|---|
| 4,542,459 A * | 9/1985 | Riederer | 600/431 |
| 5,644,613 A * | 7/1997 | Mick | 378/98.12 |
| 7,734,328 B2 | 6/2010 | Vaillant et al. | |
| 8,090,171 B2 * | 1/2012 | Kramp et al. | 382/128 |
| 2003/0120151 A1 * | 6/2003 | Constantinides | 600/431 |
| 2006/0116582 A1 * | 6/2006 | Yoshida et al. | 600/458 |
| 2008/0051648 A1 * | 2/2008 | Suri et al. | 600/407 |
| 2008/0154122 A1 | 6/2008 | Vaillant et al. | |
| 2009/0103681 A1 * | 4/2009 | Kramp et al. | 378/98.12 |
| 2009/0185730 A1 * | 7/2009 | Baumgart et al. | 382/130 |
| 2010/0053209 A1 * | 3/2010 | Rauch et al. | 345/619 |
| 2010/0158341 A1 * | 6/2010 | Baumgart | 382/132 |
| 2010/0172556 A1 * | 7/2010 | Cohen et al. | 382/128 |
| 2010/0290693 A1 * | 11/2010 | Cohen et al. | 382/134 |
| 2011/0235885 A1 * | 9/2011 | Rauch et al. | 382/131 |

OTHER PUBLICATIONS

Co-pending U.S. Appl. No. 13/076,674, filed Mar. 31, 2011.

* cited by examiner

*Primary Examiner* — Tsung-Yin Tsai
(74) *Attorney, Agent, or Firm* — Peter R. Withstandley

(57) ABSTRACT

A data management system automatically manages image buffers to produce images for angiography using a first memory portion, a second memory portion and an image data processor. The first memory portion stores first image frame data representing minimum luminance values of individual pixels of a sequence of medical images. The second memory portion stores second image frame data comprising a difference between the minimum luminance values and corresponding maximum luminance values. The image data processor processes data representing an acquired X-ray image frame of a catheterized vessel using a stored frame of maximum or minimum pixel luminance values and the second image frame data to provide an image with enhanced visualization of a catheter in a vessel.

15 Claims, 4 Drawing Sheets

DATA MANAGEMENT SYSTEM FOR USE IN ANGIOGRAPHIC X-RAY IMAGING

This is a non-provisional application of provisional application Ser. No. 61/411,026 filed Nov. 8, 2010, by J. Baumgart et al.

FIELD OF THE INVENTION

This invention concerns a data management system for use in Angiographic X-ray imaging using maximum and minimum pixel luminance values occurring in a sequence of images to provide an image with enhanced visualization of a catheter in a vessel.

BACKGROUND OF THE INVENTION

Roadmapping is a term used to refer to a special type of angiographic fluoroscopy including multiple phases. In a first phase, acquired X-ray images are displayed as acquired without performing any image subtraction while a radiation dose applied to a patient is regulated. During a second phase, a contrast agent is injected into patient vasculature and a roadmapping mask image is generated by subtracting an image of anatomic background information from a sequence of image frames acquired with contrast agent introduced into vasculature and accumulated over the image sequence. During a third phase, a roadmapping mask image is used to guide the physician during an x-ray imaging examination without further contrast agent injection.

In known systems, in order to support a roadmap mode, an image post processing system such as the system of FIG. 1, acquires images in a first phase 11 and employs a temporary internal storage buffer 12 in which a mask frame is built using minimum gray luminance values of pixels of the acquired images during the second phase. At the end of the second phase the mask frame is moved to permanent storage 14 from the temporary storage so that an internal storage buffer can be used for other intermediate image processing functions. At the start of the third phase, the mask frame is read back to the internal buffer to be used as a mask frame that is subtracted from a live fluoroscopic image during third phase 16 to give a roadmap image. Known systems involve transfer latencies and delay in transferring image data between permanent storage locations of intermediate result buffers and memory accessible by image processing hardware. A system according to invention principles addresses these deficiencies and related problems.

SUMMARY OF THE INVENTION

A system automatically manages image buffers to produce images for angiographic X-ray roadmapping. A data management system used in Angiographic X-ray imaging comprises a first memory portion, a second memory portion and an image data processor. The first memory portion stores first image frame data representing minimum luminance values of individual pixels of a sequence of medical images acquired during introduction of a contrast agent into patient vasculature. An individual pixel minimum luminance value is substantially the lowest pixel value of multiple pixel values for a particular pixel position occurring in the sequence of medical images. The second memory portion stores second image frame data comprising a difference between the minimum luminance values and corresponding maximum luminance values. The maximum luminance values comprise maximum luminance values of individual pixels of the sequence of medical images. An individual pixel maximum luminance value is substantially the highest pixel value of the multiple pixel values for a particular pixel position occurring in the sequence of medical images. The image data processor processes data representing an acquired X-ray image frame of a catheterized vessel using the second image frame data to provide an image with enhanced visualization of a catheter in a vessel.

DETAILED DESCRIPTION OF THE INVENTION

Definitions

Minimum gray luminance value comprises the darkest of the pixel luminance values being compared. Typically, the comparison is performed between two or more pixels at substantially the same corresponding locations in two or more temporally related images.

Maximum gray luminance value comprises the lighter of the pixel luminance values being compared. Typically, the comparison is performed between two or more pixels at substantially the same corresponding locations in two or more temporally related images.

DSA (Digital Subtraction Angiography) Mask comprises a frame representing anatomic background detail that is to be subtracted from another frame that additionally contains contrast agent.

Roadmap Mask is an image frame that is the result of a DSA subtraction and accumulation of contrast agent across temporally related frames that is used as a map of the vasculature for guidance of an instrument during an intervention.

Vessel Map Enhancement comprises different types of filtering that is applied to a roadmap mask to enhance the appearance of the vessels in the mask to advantageously provide a filtered roadmap mask during a third phase of roadmapping.

Figure 1:
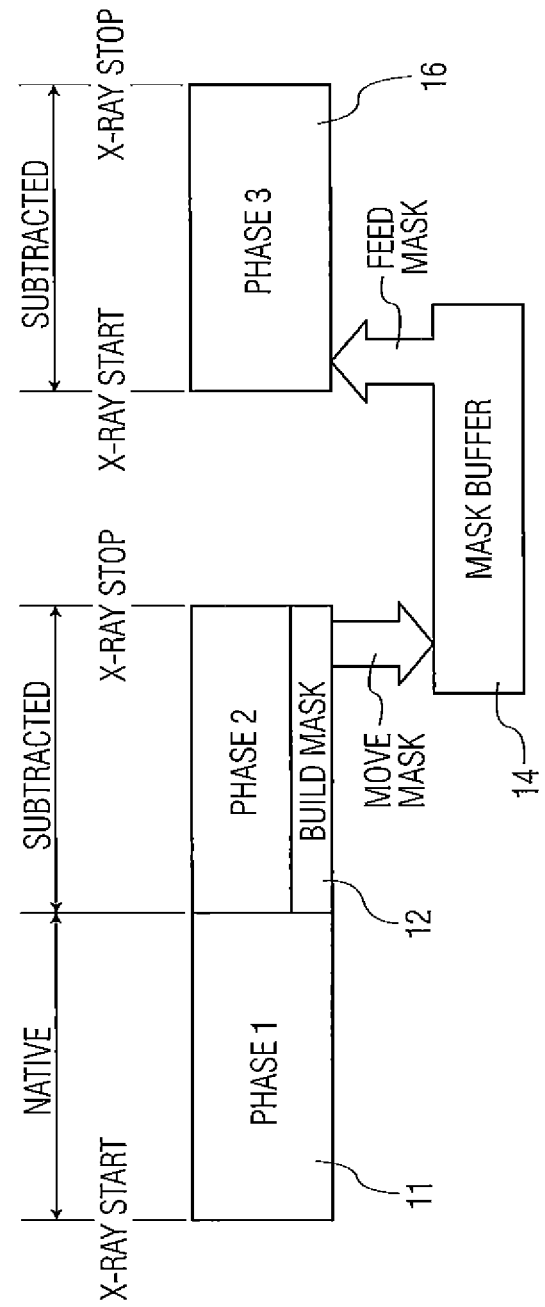
FIG. 1 shows a known roadmap workflow system for buffering images used in Angiographic roadmapping.
Figure 2:
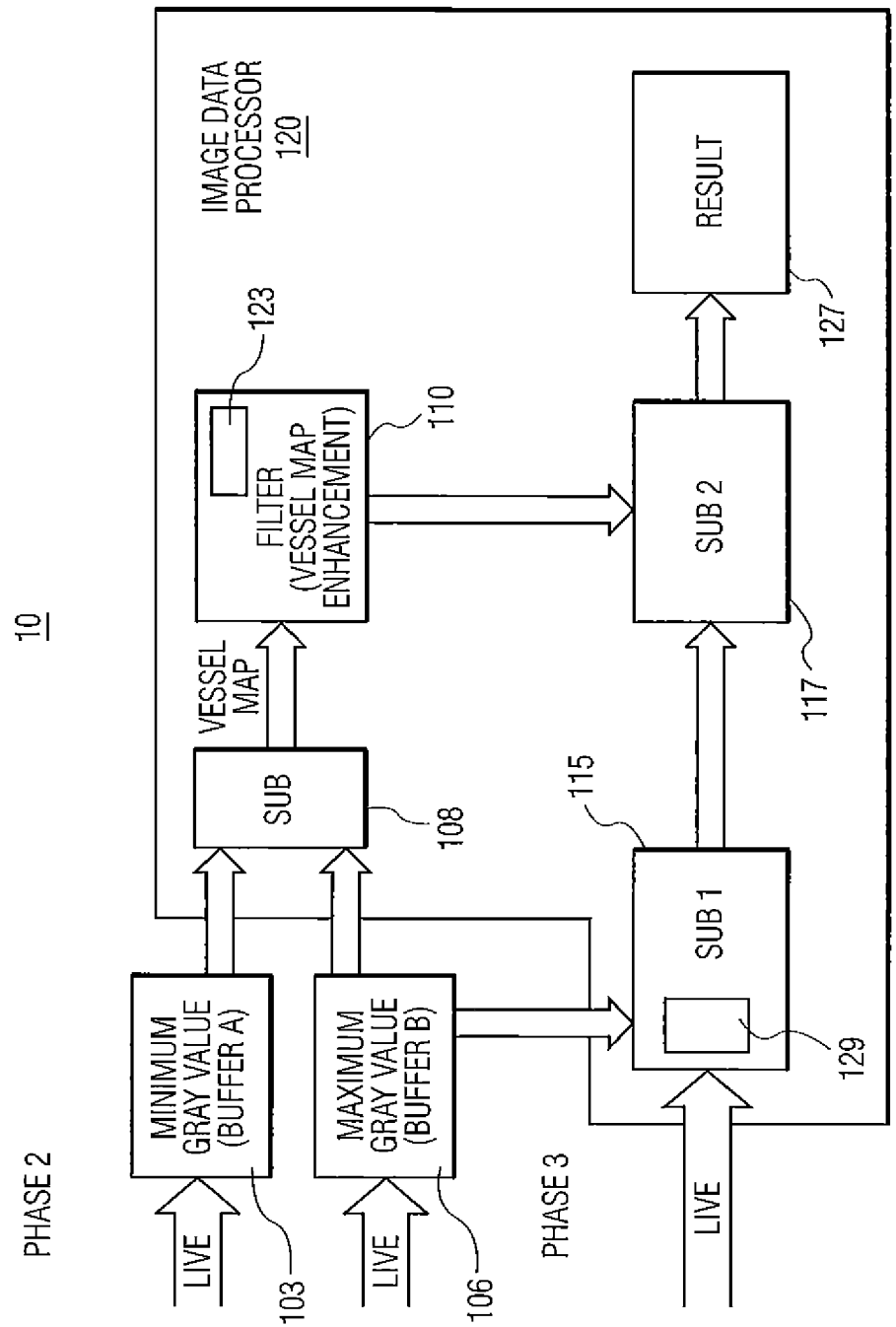
FIG. 2 shows a data management system for use in Angiographic X-ray imaging including a roadmap workflow system for buffering images minimizing transfer latencies, according to invention principles.

A data management system automatically manages image buffers to produce images for angiography using a first memory portion, a second memory portion and an image data processor. The system generates a roadmapping mask image by subtracting anatomic background information from a sequence of images acquired with contrast agent introduced and accumulated over the image sequence. FIG. 2 shows data management system 10 for use in Angiographic X-ray imaging including a roadmap workflow system for buffering images minimizing transfer latencies. System 10 acquires a sequence of images of a portion of patient anatomy in a first roadmapping phase. System 10 during a second roadmapping phase in which a contrast agent is injected into patient vasculature, provides an improved roadmap workflow by processing an individual image of the acquired image sequence by generating an image in frame buffer 103 comprising minimum gray luminance values of pixels of the image sequence including the individual image.

System 10 during the second roadmapping phase, processes the individual image by generating an image in frame buffer 106 (a first memory portion) comprising maximum gray luminance values of pixels of the image sequence including the individual image. Image data processor 120 using subtractor 108, subtracts the minimum gray luminance values of individual pixels of buffer 103 from the maximum gray luminance values of spatially corresponding pixels in buffer 106 to provide difference image data. Image data processor 120 filters 110 and stores in a second memory portion 123 the difference image data as an initial vessel map for use in providing an image with enhanced visualization of a catheter in a vessel. At the end of the second roadmapping phase, image data processor 120 advantageously overwrites the contents of image buffer 103 with the filtered difference image data comprising a vessel map in second memory portion 123. Processor 120 copies the vessel map out of image buffer 103 for additional processing (e.g., filtering) that otherwise may not be completed before start of a third roadmapping phase and schedules additional processing of the vessel map.

Processor 120 initializes processing for live fluoroscopic imaging in a third roadmapping phase by determining and storing maximum gray luminance values of pixels of the image sequence in frame buffer 106 if an intervening action invalidated the data in buffer 106. Processor 120 overwrites the contents of image buffer 103 with the filtered difference image data comprising a vessel map in second memory portion 123 if an intervening action invalidated the contents of buffer 103. Processor 120 loads a live fluoroscopic image frame in live frame buffer 129 in the third phase and locks both buffers 103 and 106 to prevent them being overwritten and during live fluoroscopic imaging performs subtraction steps 115 and 117 involving live frame 129 and the internal buffers 103 and 106 to produce an end result.

Processor 120 subtracts maximum gray luminance values of individual pixels of the image sequence in frame buffer 106 from luminance data of spatially corresponding individual pixels of a live fluoroscopic image frame in a subtraction in step 115 to provide a first result frame. Processor 120 further subtracts individual pixel luminance values of the difference image data from pixel luminance data of spatially corresponding individual pixels of the first result frame in a subtraction in step 117 to provide enhanced visualization image 127. System 10 provides an improved image vessel roadmap workflow that employs an advantageous buffering scheme for images used in roadmapping to minimize transfer latencies between permanent storage locations of intermediate result buffers and memory accessible by image processing hardware. Processor 120 unlocks buffers 103 and 106.

For each received subsequent live fluoroscopic image frame, the third phase is repeated. During a single X-ray event, buffers 103 and 106 do not become invalidated by an intervening action and are not reloaded. Between acquired frames of an X-ray procedure, additional image data post-processing operations employing additional temporary storage that are performed on the vessel map starting at the end of phase 2 may finish. The additional temporary storage in different embodiments may comprise an image frame buffer or reduced memory storage such as for line by line processing of an image, for example. The frame resulting from the additional processing is reloaded into buffer 103 when it is unlocked after processing of a current frame has completed.

Figure 3:
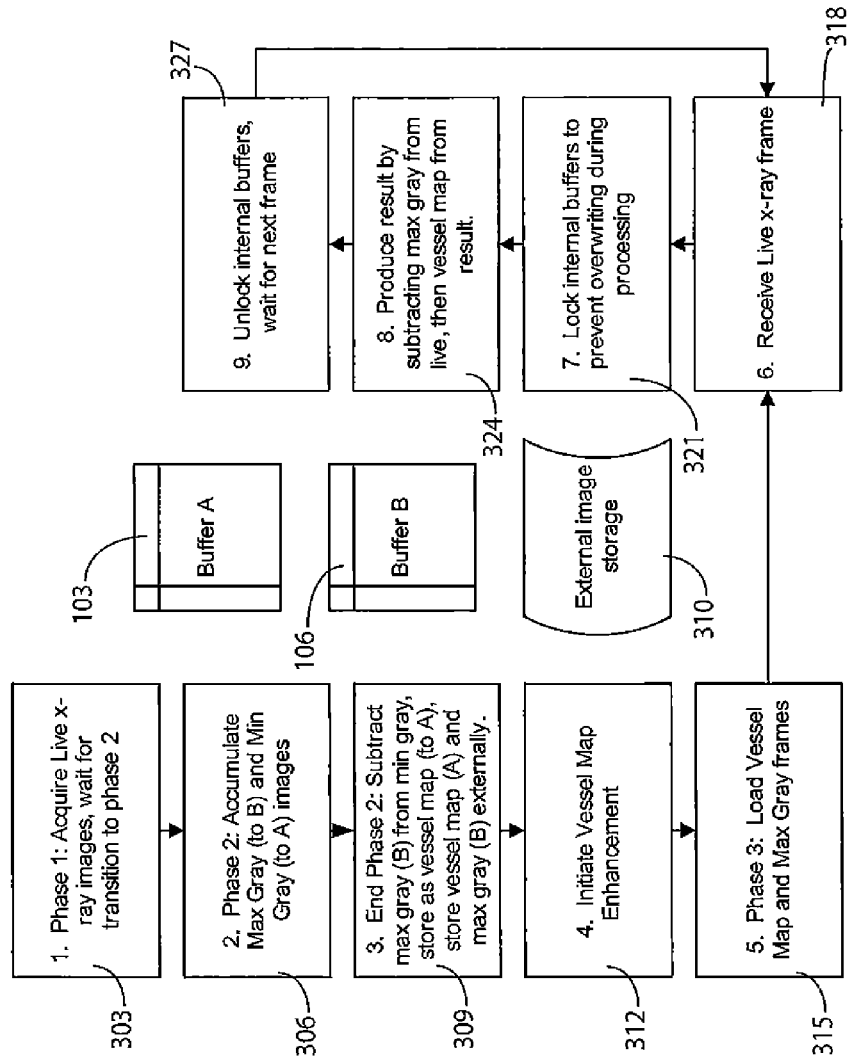
FIG. 3 shows a flowchart of a process for use in Angiographic X-ray imaging including a roadmap workflow for providing an image with enhanced visualization of a catheter in a vessel, according to invention principles.

FIG. 3 shows a flowchart of a process for use in Angiographic X-ray imaging employed by roadmap workflow system 10 (FIG. 2) for providing an image with enhanced visualization of a catheter in a vessel. System 10 in step 303 in a first roadmapping phase acquires a sequence of live X-ray images. System 10 in step 306, in a second roadmapping phase, generates an image in frame buffer 103 comprising minimum gray luminance values of pixels of the image sequence by determining a minimum luminance value of each individual pixel position of the images of the sequence. System 10 in step 306, in a second roadmapping phase, also generates an image in frame buffer 106 comprising maximum gray luminance values of pixels of the image sequence by determining a maximum luminance value of each individual pixel position of the images of the sequence. At the end of the second roadmapping phase image data processor in step 309 subtracts the minimum gray luminance values of individual pixels of buffer 103 from the maximum gray luminance values of spatially corresponding pixels in buffer 106 to provide difference image data comprising a vessel map and stores the vessel map in external image storage 310.

In step 312 image data processor 120 initiates vessel map enhancement including by filtering and contrast enhancement, for example, and stores the enhanced map in buffer 103. In step 315, processor 120 loads the vessel map in buffer 103 and maximum gray luminance values of pixels of the image sequence in buffer 106 for performing the third roadmapping phase to provide an enhanced visualization image. Image data processor 120 receives a live X-ray image in step 318 and in step 321 locks internal buffers 103 and 106 preventing overwriting the image data in the buffers during subsequent image data processing. In step 324, processor 120 subtracts maximum gray luminance values of individual pixels of the image sequence in frame buffer 106 from luminance data of spatially corresponding individual pixels of the received live fluoroscopic image and further subtracts individual pixel luminance values of the difference image data. Processor 120 unlocks buffers 103 and 106 and waits for a next live X-ray image frame in step 318 and repeats steps 318 to 327 for roadmapping phase three for each received live X-ray image frame.

Figure 4:
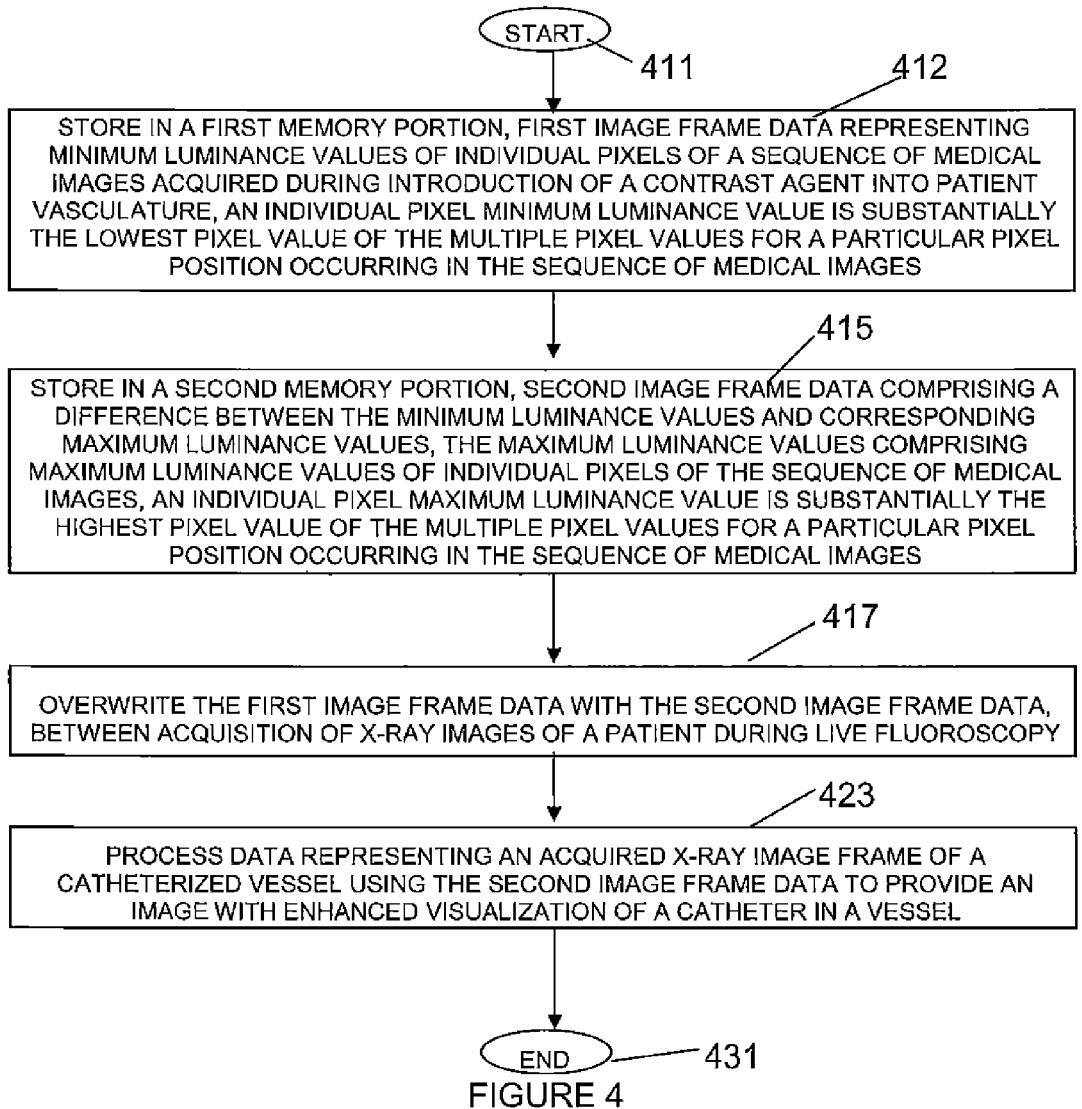
FIG. 4 shows a flowchart of a process used by a data management system for Angiographic X-ray imaging including a roadmap workflow minimizing transfer latencies, according to invention principles.

FIG. 4 shows a flowchart of a process used by data management system 10 (FIG. 2) for use in Angiographic X-ray imaging including a roadmap workflow for minimizing transfer latencies. In step 412 following the start at step 411, image data processor 120 stores in first memory portion 103, first image frame data representing minimum luminance values of individual pixels of a sequence of medical images acquired during introduction of a contrast agent into patient vasculature. An individual pixel minimum luminance value is substantially the lowest pixel value of the multiple pixel values for a particular pixel position occurring in the sequence of medical images. In step 415 image data processor 120 stores in second memory portion 106, second image frame data comprising a difference between the minimum luminance values and corresponding maximum luminance values. The maximum luminance values comprise maximum luminance values of individual pixels of the sequence of medical images. An individual pixel maximum luminance value is substantially the highest pixel value of the multiple pixel values for a particular pixel position occurring in the sequence of medical images.

Image data processor 120 in step 417 overwrites the first image frame data with the second image frame data and stores the second image frame data in the first memory portion 103, in response to generation of the second image frame data, between acquisition of X-ray images of a patient during live fluoroscopy. Processor 120 filters the second image frame data acquired from the first memory portion 103 for use in providing the image with enhanced visualization of the catheter in the vessel. In step 423, processor 120 processes data representing an acquired X-ray image frame of a catheterized vessel using the second image frame data to provide an image with enhanced visualization of a catheter in a vessel. Processor 120 subtracts data representing a frame of the maximum luminance values and the second image frame from the data representing the acquired X-ray image frame, to provide the image with enhanced visualization of the catheter in the vessel. In another embodiment processor 120 subtracts data representing a frame of the minimum luminance values and the second image frame from the data representing the acquired X-ray image frame, to provide the image with enhanced visualization of the catheter in the vessel. For each acquired X-ray image frame of a sequence of image frames of a catheterized vessel, processor 120 stores first image frame data and second image frame data and processes data representing an acquired X-ray image frame of a catheterized vessel to provide an image with enhanced visualization data of the catheter in the vessel. The process of FIG. 4 terminates at step 431.

A processor as used herein is a device for executing machine-readable instructions stored on a computer readable medium, for performing tasks and may comprise any one or combination of hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 2-4 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A data management system automatically manages image buffers to produce images for angiography minimizing transfer latencies. Further, the processes and applications may, in alternative embodiments, be located on one or more (e.g., distributed) processing devices on a network linking the units of FIG. 2. Any of the functions and steps provided in FIGS. 2-4 may be implemented in hardware, software or a combination of both.

What is claimed is:

1. A data management system for use in Angiographic X-ray imaging, comprising:
   a first memory portion for storing first image frame data representing minimum luminance values of individual pixels of a sequence of medical images acquired during introduction of a contrast agent into patient vasculature, an individual pixel minimum luminance value is substantially the lowest pixel value of the plurality of pixel values for a particular pixel position occurring in said sequence of medical images;
   a second memory portion for storing second image frame data comprising a difference between said minimum luminance values and corresponding maximum luminance values, said maximum luminance values comprising maximum luminance values of individual pixels of said sequence of medical images, an individual pixel maximum luminance value is substantially the highest pixel value of the plurality of pixel values for a particular pixel position occurring in said sequence of medical images; and
   an image data processor for processing data representing an acquired X-ray image frame of a catheterized vessel using said second image frame data to provide an image with enhanced visualization of a catheter in a vessel.

2. A system according to claim 1, wherein
   said image data processor processes data representing said acquired X-ray image frame of the catheterized vessel by subtracting data representing a frame of said maximum luminance values and said second image frame from said data representing said acquired X-ray image frame, to provide said image with enhanced visualization of said catheter in said vessel.

3. A system according to claim 1, wherein
   said image data processor processes data representing said acquired X-ray image frame of the catheterized vessel by subtracting data representing a frame of said minimum luminance values and said second image frame from said data representing said acquired X-ray image frame, to provide said image with enhanced visualization of said catheter in said vessel.

4. A system according to claim 1, wherein
said image data processor stores said second image frame data in said first memory portion, in response to generation of said second image frame data.

5. A system according to claim 4, wherein
said image data processor overwrites said first image frame data with said second image frame data, between acquisition of X-ray images of a patient during live fluoroscopy.

6. A system according to claim 1, wherein
said image data processor, for each acquired X-ray image frame of a sequence of image frames of Hall the catheterized vessel, stores first image frame data and second image frame data and processes data representing an acquired X-ray image frame of the catheterized vessel to provide an image with enhanced visualization data of said catheter in said vessel.

7. A system according to claim 1, wherein
said image data processor stores said second image frame data in said first memory portion, in response to generation of said second image frame data and
filters said second image frame data acquired from said first memory portion for use in providing said image with enhanced visualization of said catheter in said vessel.

8. A method for managing data for use in Angiographic X-ray imaging, comprising the activities:
    storing in a first memory portion, first image frame data representing minimum luminance values of individual pixels of a sequence of medical images acquired during introduction of a contrast agent into patient vasculature, an individual pixel minimum luminance value is substantially the lowest pixel value of the plurality of pixel values for a particular pixel position occurring in said sequence of medical images;
    storing in a second memory portion, second image frame data comprising a difference between said minimum luminance values and corresponding maximum luminance values, said maximum luminance values comprising maximum luminance values of individual pixels of said sequence of medical images, an individual pixel maximum luminance value is substantially the highest pixel value of the plurality of pixel values for a particular pixel position occurring in said sequence of medical images; and
    processing data representing an acquired X-ray image frame of a catheterized vessel using said second image frame data to provide an image with enhanced visualization of a catheter in a vessel.

9. A method according to claim 8, including the activity of
overwriting said first image frame data with said second image frame data, between acquisition of X-ray images of a patient during live fluoroscopy.

10. A method according to claim 8, including the activity of
subtracting data representing a frame of said maximum luminance values and said second image frame from said data representing said acquired X-ray image frame, to provide said image with enhanced visualization of said catheter in said vessel.

11. A method according to claim 8, including the activity of
subtracting data representing a frame of said minimum luminance values and said second image frame from said data representing said acquired X-ray image frame, to provide said image with enhanced visualization of said catheter in said vessel.

12. A method according to claim 8, including the activity of
storing said second image frame data in said first memory portion, in response to generation of said second image frame data.

13. A method according to claim 8, including the activity of
for each acquired X-ray image frame of a sequence of image frames of Rail the catheterized vessel, stores first image frame data and second image frame data and processes data representing an acquired X-ray image frame of the catheterized vessel to provide an image with enhanced visualization data of said catheter in said vessel.

14. A method according to claim 8, including the activities of
    storing said second image frame data in said first memory portion, in response to generation of said second image frame data and
    filtering said second image frame data acquired from said first memory portion for use in providing said image with enhanced visualization of said catheter in said vessel.

15. A method for managing data for use in Angiographic X-ray imaging, comprising the activities:
    storing in a first memory portion, first image frame data representing minimum luminance values of individual pixels of a sequence of medical images acquired during introduction of a contrast agent into patient vasculature, an individual pixel minimum luminance value is substantially the lowest pixel value of the plurality of pixel values for a particular pixel position occurring in said sequence of medical images;
    storing in a second memory portion, second image frame data comprising a difference between said minimum luminance values and corresponding maximum luminance values, said maximum luminance values comprising maximum luminance values of individual pixels of said sequence of medical images, an individual pixel maximum luminance value is substantially the highest pixel value of the plurality of pixel values for a particular pixel position occurring in said sequence of medical images;
    overwriting said first image frame data with said second image frame data, between acquisition of X-ray images of a patient during live fluoroscopy; and
    processing data representing an acquired X-ray image frame of a catheterized vessel using said second image frame data to provide an image with enhanced visualization of a catheter in a vessel.

* * * * *